United States Patent
Rizoiu

(10) Patent No.: US 6,533,775 B1
(45) Date of Patent: Mar. 18, 2003

(54) LIGHT-ACTIVATED HAIR TREATMENT AND REMOVAL DEVICE

(76) Inventor: Ioana M. Rizoiu, 19 New York Ct., Dana Point, CA (US) 92624

( * ) Notice: Subject to any disclaimer, the term of this patent is extended or adjusted under 35 U.S.C. 154(b) by 0 days.

(21) Appl. No.: 09/566,209

(22) Filed: May 5, 2000

Related U.S. Application Data

(60) Provisional application No. 60/132,610, filed on May 5, 1999.

(51) Int. Cl.[7] .............................................. A61B 18/18
(52) U.S. Cl. .............................. 606/9; 30/34.1; 30/538; 607/89
(58) Field of Search ............................ 606/9, 2, 10, 1, 606/12, 3; 424/73; 30/32, 140, 123.3, 34.1, 538; 607/88, 89

(56) References Cited

U.S. PATENT DOCUMENTS

| | | | |
|---|---|---|---|
| 4,631,064 A | 12/1986 | Juneja | 8/161 |
| 4,819,669 A | 4/1989 | Politzer | 132/200 |
| 5,065,515 A | 11/1991 | Iderosa | 30/140 |
| 5,182,857 A | * 2/1993 | Simon | 132/118 |
| 5,226,907 A | * 7/1993 | Tankovich | 606/131 |
| 5,402,697 A | 4/1995 | Brooks | 83/18 |
| 5,752,949 A | * 5/1998 | Tankovich et al. | 606/133 |
| 5,902,574 A | 5/1999 | Stoner et al. | 424/73 |
| 6,187,001 B1 | 2/2001 | Azar et al. | 606/9 |

FOREIGN PATENT DOCUMENTS

GE        29611519.3        * 10/1996

* cited by examiner

Primary Examiner—Michael Peffley
(74) Attorney, Agent, or Firm—Stout, Uxa, Buyan and Mullins, LLP

(57) ABSTRACT

A device for disrupting hair growth includes an applicator sized and configured to be held in a hand of a user for shaving, and a source of electromagnetic energy constructed to emit electromagnetic energy having an energy density of between about 0.1 J/cm$^2$ and about 15 J/cm$^2$ and, more preferably, between about 0.1 J/cm$^2$ and 1 J/cm$^2$. The device further includes a blade affixed to the applicator, the blade being constructed to fit smoothly against and to be swept over a skin surface that has been subjected to the emitted electromagnetic energy from the source of electromagnetic energy, to thereby mechanically remove hair from the skin surface.

32 Claims, 2 Drawing Sheets

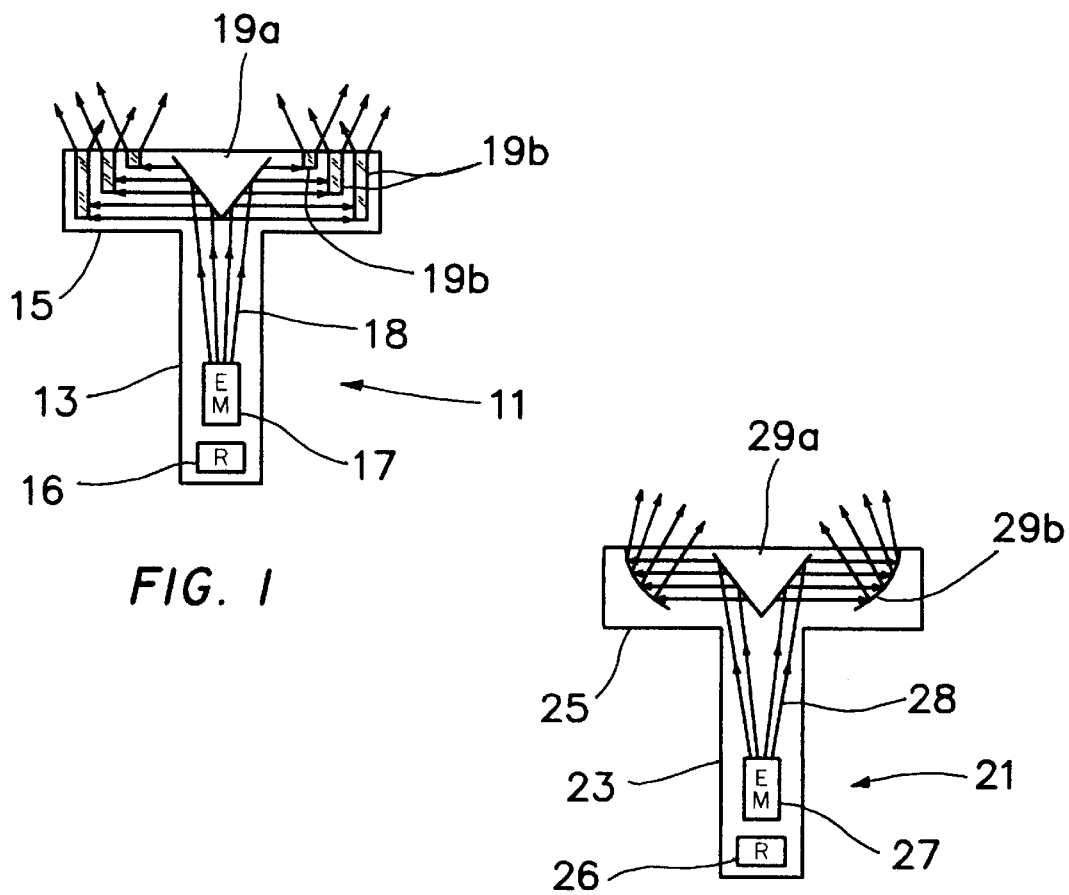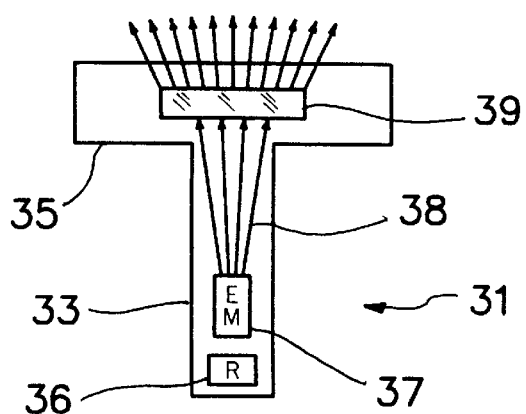

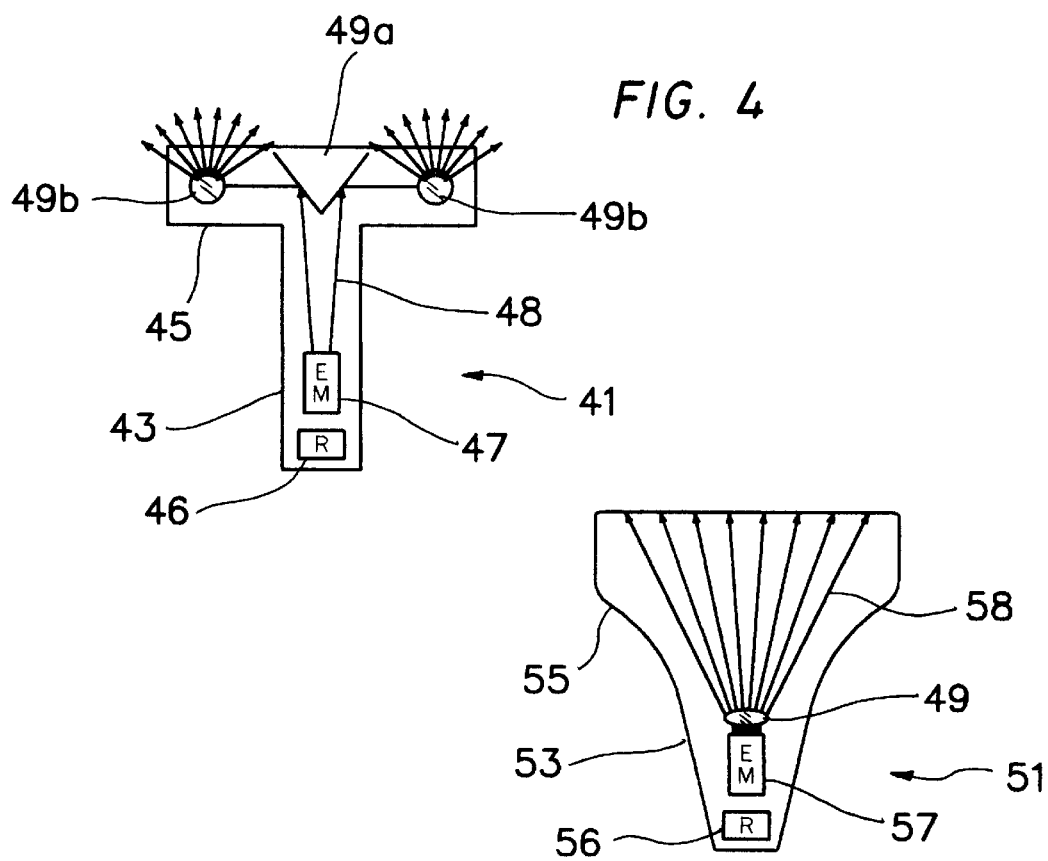
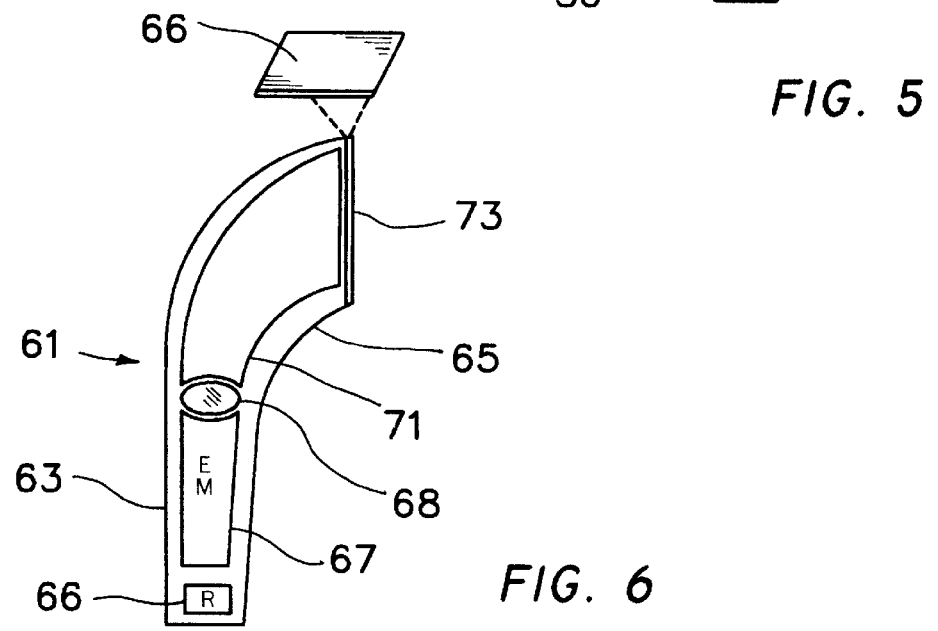

LIGHT-ACTIVATED HAIR TREATMENT AND REMOVAL DEVICE

This application claims the benefit of U.S. Provisional Application No. 60/132,610 filed May 5, 1999.

BACKGROUND OF THE INVENTION

1. Field of the Invention

The present invention relates to an apparatus using an electromagnetic energy source, which in combination with a specialized cream can reduce or remove body hair.

2. Description of Related Art

The conventional methods and devices which are currently used to remove body hair are: depilatory wax, depilatory cream and shaving appliances using razor blades. Each one of these methods/appliances includes one or more limitations. For example, the depilatory wax is a time consuming, painful and difficult methodology to remove hair. The wax is actually utilized to pull the hair shaft from within the skin. The user is required to heat-up the wax, place the wax onto the skin, apply cotton sheets over the layer of wax, wait a few moments and pull quickly the sheets with the attached wax and embedded hair shafts. The procedure is repeated for every surface where the hair has to be removed.

In the case of the depilatory creams, the hair is chemically decomposed by the cream after it is applied for 10 to 15 minutes to the hair on the skin. Skin irritation and exfoliation may in some instances result from prolonged contact of the skin to the reactive cream.

Shaving devices with blades remove hair through the cutting action of the blade. The blades are sharp and many times produce skin cuts, which can increase the likelihood of infection.

Recently, Tankovich in U.S Pat. No. 5,871,480 disclosed a method of removing hair by applying a cream to the skin area and exposing the skin area to a specific frequency of electromagnetic energy. Although this method may be advantagegous relative to the other methods, it still may present certain drawbacks. As an example, the steps required in this patent may be cumbersome and may require an excessive amount of time. For instance, the method requires a passage of about 20 minutes of time after the application of the cream to the skin area, before a source of electromagnetic energy may be applied to that skin area.

There continues to be a need for better methods and devices to quickly, conveniently, effectively and safely remove hair.

SUMMARY OF THE INVENTION

The present invention provides for an improved method and system which is fast and effective for removing body hair. In accordance with one aspect of the present invention, a device for disrupting hair growth includes an applicator sized and configured to be held in a hand of a user for shaving, and a source of electromagnetic energy constructed to emit electromagnetic energy having an energy density of between about 0.1 $J/cm^2$ and about 15 $J/cm^2$. The device further includes a blade affixed to the applicator, the blade being constructed to fit smoothly against and to be swept over a skin surface that has been subjected to the emitted electromagnetic energy from the source of electromagnetic energy, to thereby mechanically remove hair from the skin surface. In accordance with another aspect of the present invention, the source of electromagnetic energy is constructed to emit electromagnetic energy having an energy density of between about 0.1 $J/cm^2$ and about 1 $J/cm^2$. The blade can comprise a dull non-metallic blade or a razor blade, and the source of electromagnetic energy can be constructed to emit electromagnetic energy which is substantially free of light that would cause heating of the skin.

The device can include a reservoir filled with a composition for disrupting hair cuticles, which are the outside coverings of hairs. In accordance with one aspect of the invention the composition comprises a thiol component and a ceteareth component. In another embodiment the composition comprises NAIR®.

A method for disrupting hair growth on a mammal in accordance with the present invention includes a step of introducing a composition onto a skin surface, wherein the composition comprises at least one of a thiol component and a ceteareth component, and includes another step of applying electromagnetic energy to the skin surface where the composition has been introduced, the electromagnetic energy having an energy density between about 0.1 $J/cm^2$ and about 15 $J/cm^2$ and, more preferably, between about 0.1 $J/cm^2$ and about 1 $J/cm^2$. The electromagnetic energy is applied for a duration of at least three seconds and the electromagnetic energy reacts with the composition to cause at least partial disruption of hair follicles or hair cuticles on the skin surface. A subsequent step of the method includes a step of mechanically removing hair from the skin surface.

The step of introducing a composition onto a skin surface can comprise a step of introducing a composition comprising a thiol component and a ceteareth component, or can comprise a step of introducing a composition comprising a thiol component, a ceteareth component, water, a lubricant, a hydroxide component, a moisturizer, an aloe component and a fragrance. The step of mechanically removing hair from the skin surface can comprise a step of removing hair from the skin surface with a razor blade, and the lubricant can comprise a mineral oil. In accordance with one aspect of the present invention, the hydroxide component can comprise at least one of a metal hydroxide, a sodium hydroxide, calcium hydroxide and a cetearylalcohol.

The thiol component can comprise at least one of a metal thioglycolate, a calcium thioglycolate, a sodium thioglycolate and a potassium thioglycolate, and the ceteareth component can comprise at least one of a cetearylalcohol and a ceteareth-20. Furthermore, the moisturizer can comprise lanolin, and the aloe component can comprise at least one of an aloe juice, an aloe extract, and an aloe vera gel. In accordance with one aspect of the method, the composition is NAIR®, which comprises water, a mineral oil, a calcium hydroxide, a ceaterylalcohol, a calcium thioglycolate, a sodium thioglycolate, a ceteareth-20, a lanolin, an aloe juice and a fragrance. The composition can further comprise at least one of the following: a sodium silicate, a stearyl alcohol, a squalane, a tocopheryl acetate (vitamin E), an avocado oil, a jojoba oil, a bisabol, a sodium lauryl sulfate, a urea, and an iron oxide.

The present invention, together with additional features and advantages thereof, may best be understood by reference to the following description taken in connection with the accompanying illustrative drawings.

BRIEF DESCRIPTION OF THE DRAWINGS

FIG. 1 is a cross-sectional view of a shaving device having a beam splitter and diffraction elements in accordance with a first embodiment of the present invention;

FIG. 2 is a cross-sectional view of a shaving device having a beam splitter and reflecting elements in accordance with a second embodiment of the present invention;

FIG. 3 is a cross-sectional view of a shaving device having a diffuser in accordance with a third embodiment of the present invention;

FIG. 4 is a cross-sectional view of a shaving device having a beam splitter and diffusers in accordance with a fourth embodiment of the present invention;

FIG. 5 is a cross-sectional view of a shaving device having divergent optics in accordance with a fifth embodiment of the present invention; and FIG. 6 is a side-elevation view of a shaving device of the present invention.

DETAILED DESCRIPTION OF THE PRESENTLY PREFERRED EMBODIMENTS

Referring more particularly to the drawings, a shaving device 11 is shown in FIG. 1 comprising a handle 13 and a shaving head 15. The shaving device 11 further comprises a reservoir 16 filled with a depilatory cream or composition. As can be seen from the cross-sectional view, the handle 13 incorporates a source of electromagnetic energy 17 that can comprise, for example, in any of the embodiments of FIGS. 1–6, a light emitting diode (LED), a laser, or a lamp. The source of electromagnetic energy 17 emits electromagnetic energy 18, which is transmitted into the shaving head 15 through optical guides which are transparent to the specific electromagnetic energy wavelength. The electromagnetic energy emitted from the shaving devices of FIGS. 1–6 preferably has an energy density of between about 0.1 $J/cm^2$ and about 15 $J/cm^2$ and, more preferably, between about 0.1 $J/cm^2$ and about 1 $J/cm^2$. In one embodiment, the source of electromagnetic energy is constructed to emit electromagnetic energy which is substantially free of IR light to thereby attenuate heating of the skin. The shaving head 15 comprises a beam splitter 19a and diffraction elements 19b which reflect and refract the electromagnetic energy beam in the direction of the target. The electromagnetic energy from the shaving device 11 is transferred to a cream with depilatory and/or bleaching properties that is applied on the hair and skin. The electromagnetic energy is emitted from the surface of the shaving head 15 facing the cream on the skin.

The electromagnetic energy may be supplied from an external source into the shaving device 11 by a fiber optic cable, for example. In the presently preferred embodiment, the electromagnetic energy is generated within the shaving device 11 and directed through the shaving head 15 to the target surface facing and/or contacting the cream. The power source may comprise batteries or a power cord.

FIG. 2 is a cross-sectional view of a shaving device 21 comprising a handle 23 and a shaving head 25 in accordance with a second embodiment of the present invention. The shaving device 21 further comprises a reservoir 26 filled with a depilatory cream or composition. The handle 23 incorporates a source of electromagnetic energy 27 that emits electromagnetic energy 28 for transmission into the shaving head 25. The shaving head 25 comprises a beam splitter 29a and reflecting optics or surfaces 29b which split and reflect the electromagnetic energy beam in the direction of the target.

FIG. 3 is a cross-sectional view of a shaving device 31 in accordance with a third embodiment of the present invention, comprising a handle 33 and a shaving head 35. The shaving device 31 further comprises a reservoir 36 filled with a depilatory cream or composition. The handle 33 incorporates a source of electromagnetic energy 37 that emits electromagnetic energy 38 for transmission into the shaving head 35. The shaving head 35 comprises a diffraction element or diffusor 39 which refract or diffuse the electromagnetic energy beam in the direction of the target.

FIG. 4 is a cross-sectional view of a shaving device 41 in accordance with a fourth embodiment of the present invention, comprising a handle 43 and a shaving head 45. The shaving device 41 further comprises a reservoir 46 filled with a depilatory cream or composition. The handle 43 incorporates a source of electromagnetic energy 47 that emits electromagnetic energy 48 for transmission into the shaving head 45. The shaving head 45 comprises a beam splitter 49a and diffusers 49b which split and diffuse the electromagnetic energy beam in the direction of the target.

FIG. 5 is a cross-sectional view of a shaving device 51 in accordance with a fifth embodiment of the present invention, comprising a handle 53 and a shaving head 55. The shaving device 51 further comprises a reservoir 56 filled with a depilatory cream or composition. The handle 53 incorporates a source of electromagnetic energy 57 that emits electromagnetic energy 58 for transmission into the shaving head 55. The shaving head 55 comprises a divergent optic 49 which diverges and directs the electromagnetic energy beam in the direction of the target.

FIG. 6 is a side-elevation view of a shaving device 61 of the present invention, comprising a handle 63 and a shaving head 65, which is constructed to accommodate a blade 66. The shaving device 61 further comprises a reservoir 64 filled with a depilatory cream or composition. The handle 63 incorporates a source of electromagnetic energy 67 that emits electromagnetic energy for transmission through a coupling optic 68, a light pipe 71, and a frosted-surface light diffuser 73 in the direction of the target. When the blade 66, which can comprise a dull non-metallic blade or a razor blade, is affixed to the shaving head 65, the blade 66 fits smoothly against and can be swept over a skin surface that has been subjected to electromagnetic energy from the source of electromagnetic energy 67, to thereby mechanically remove hair from the skin surface.

According to the present invention, the depilatory cream or composition is engineered to include properties for interacting with the electromagnetic energy to provide for improved (e.g., faster) depilatory results.

In one embodiment, the cream or composition comprises a thiol component. In another embodiment, the cream or composition comprises a hydroxide component, a thiol component, and a ceteareth component. In another embodiment, the composition comprises water, a lubricant, a hydroxide component, a thiol component, a ceteareth component, a moisturizer, an aloe component and a fragrance. The lubricant may comprise a mineral oil. The hydroxide component includes at least one of a metal hydroxide, a sodium hydroxide, a calcium hydroxide and a cetearylalcohol. The thiol component comprises at least one of a metal thioglycolate, a calcium thioglycolate, a sodium thioglycolate and a potassium thioglycolate. The ceteareth component comprises at least one of a cetearylalcohol and a ceteareth-20. The moisturizer comprises lanolin. The aloe component comprises at least one of an aloe juice, an aloe extract and an aloe vera gel.

In a preferred embodiment, the composition comprises water, a mineral oil, a calcium hydroxide, a ceaterylalcohol, a calcium thioglycolate, a sodium thioglycolate, a ceteareth-20, a lanolin, and an aloe juice and a fragrance. The proportions of each ingredient is similar to that of NAIR®, a hair removal product sold by Carter-Wallace, Inc. In another preferred embodiment, the composition is NAIR®.

In another embodiment, the composition further comprises sodium silicate, a stearyl alcohol, a squalane, a tocopheryl acetate (vitamin E), an avocado oil, a jojoba oil, a bisabol, a sodium lauryl sulfate, a urea, and an iron oxide.

For example, the cream may include ingredients such as mineral oils, calcium hydroxide, cetearyl alcohol, calcuim thioglycolate, sodium thioglycolate, ceteareth-20, lanolin, grangarance and plant extracts.

A role of the electromagnetic energy source is to accelerate the chemical reaction of the cream to thereby reduce the onset time. The depilatory cream may include one or more photosensitive elements or compounds which when activated by the electromagnetic eneregy provide faster and/or more effective decomposition of the hair follicle. In a different embodiment the cream may include ingredients such as hydrogen peroxide which when activated by the electromagnetic energy produces enhanced hair bleaching without substantial decomposition of the hair. In some embodiments the cream is transparent to visible electromagnetic energy and in other embodiments is opaque and selective ingredients absorb the electromagnetic energy which activates or enhances the chemical process of hair decomposition.

The present invention may overcome the limitations of the existing technology by performing one or more of the following:

I. Eliminating/reducing skin irritation;
II. Taking less time to achieve comparable or superior results;
III. Avoiding skin cuts and therefore reducing or eliminating the risk of infection; and
IV. Eliminating the pain and discomfort associated with depilatory waxing.

The cream may be wavelength-sensitive, and a wavelength of the electromagnetic energy may be matched to the wavelength to which the cream is sensitive. One or more mirrors may be oriented at 45 degree angles, for example, to the electromagnetic eneregy beam axis for directing the beam, as disclosed in U.S. Pat. No. 5,306,143, the entire contents of which are expressly incorporated herein by reference. In accordance with one aspect of the present invention, a user may hold a static electricity source or otherwise acquire a static electrical charge before or during implementation of a hair removal procedure.

A method for disrupting hair growth on a mammal in accordance with the present invention includes a step of introducing a composition onto a skin surface, wherein the composition comprises at least one of a thiol component and a ceteareth component. The method comprises another step of applying electromagnetic energy to the skin surface where the composition has been introduced, wherein the electromagnetic energy has an energy density between about 0.1 J/cm$^2$ and about 15 J/cm$^2$ and, more preferably, between about 0.1 J/cm$^2$ and about 1 J/cm$^2$. The electromagnetic energy is applied for a duration of at least three seconds and the electromagnetic energy reacts with the composition to cause at least partial disruption of hair follicles or hair cuticles (i.e., outside coverings of hairs) on the skin surface. Subsequently, hair is mechanically removed from the skin surface.

In a presently preferred embodiment, the step of introducing a composition onto a skin surface comprises a step of introducing a composition comprising both a thiol component and a ceteareth component. In accordance with another embodiment, the method comprises a step of introducing a composition comprising a thiol component, a ceteareth component, water, a lubricant, a hydroxide component, a moisturizer, an aloe component and a fragrance. The step of mechanically removing hair from the skin surface can comprise a step of removing hair from the skin surface with a razor blade. The lubricant can comprise a mineral oil. In one embodiment, the hydroxide component comprises at least one of a metal hydroxide, a sodium hydroxide, calcium hydroxide and a cetearylalcohol.

The thiol component can comprise at least one of a metal thioglycolate, a calcium thioglycolate, a sodium thioglycolate and a potassium thioglycolate, and the ceteareth component can comprise at least one of a cetearylalcohol and a ceteareth-20. The moisturizer can comprise lanolin, and the aloe component can comprise at least one of an aloe juice, an aloe extract, and an aloe vera gel. In one embodiment of the method of the present invention, the composition is NAIR®, which comprises water, a mineral oil, a calcium hydroxide, a ceaterylalcohol, a calcium thioglycolate, a sodium thioglycolate, a ceteareth-20, a lanolin, an aloe juice and a fragrance. The composition can further comprise at least one of the following: a sodium silicate, a stearyl alcohol, a squalane, a tocopheryl acetate (vitamin E), an avocado oil, a jojoba oil, a bisabol, a sodium lauryl sulfate, a urea, and an iron oxide. The step of introducing the composition can be affected by oral administration, or can be affected by topical administration.

Non-limiting Examples

A person wishes to remove hair from her legs. She applies a composition according to this invention, for example, NAIR®. Within less than about 20 minutes, preferably 4 minutes, she applies a source of electromagnetic energy in accordance with this invention. The duration of electromagnetic energy application is for about less than 20 minutes. Within about less than 1 hour, preferably less than 0.5 hour, more preferably less than 15 minutes, even more preferably less than 10 minutes, the hair is removed by wiping with a towel. The hair may also be removed by a razor.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A device for removing hair, comprising:
   an applicator sized and configured to be held in a hand of a user;
   a reservoir coupled to the applicator and constructed to hold a depilatory composition and to release the depilatory composition onto the user's skin
   an energy emission assembly coupled to the applicator and configured to apply diffused electromagnetic energy to a surface of the user's skin; and
   a blade affixed to the applicator, the blade being constructed to fit smoothly against and be swept over the surface of the skin which has been subjected to the depilatory composition and the diffused electromagnetic energy emitted by the energy emission assembly.

2. The device for removing hair according to claim 1, wherein the energy emission assembly comprises:
   an electromagnetic energy source for emitting electromagnetic energy and directing the electromagnetic energy toward a relatively small area of the surface of the skin; and
   at least one energy scattering element for receiving the electromagnetic energy from the electromagnetic energy source and redirecting the electromagnetic energy over a larger area of the surface of the skin.

3. The device for removing hair according to claim 2, wherein the at least one energy scattering element comprises;

a beam splitter positioned and configured to receive and divide the electromagnetic energy from the electromagnetic energy source; and at least one diffraction element positioned to receive the divided electromagnetic energy from the beam splitter and configured to spread the electromagnetic energy over the larger area.

4. The device for removing hair according to claim 3, wherein the at least one diffraction element comprises at least one reflecting surface.

5. The device for removing hair according to claim 3, wherein the electromagnetic energy source is a light source and wherein the at least one diffraction element comprises at least one light diffuser.

6. The device for removing hair according to claim 3, wherein the at least one diffraction element comprises at least one divergent optic.

7. The device for removing hair as set forth in claim 1, wherein the blade comprises a dull non-metallic blade.

8. The device for removing hair as set forth in claim 1, wherein the blade comprises a razor blade.

9. The device for removing hair as set forth in claim 1, wherein the reservoir is filled with a depilatory composition.

10. The device for removing hair as set forth in claim 1, wherein reservoir is filled with a composition including at least one photosensitive element.

11. The device for removing hair as set forth in claim 1, wherein the reservoir is filled with a composition including at least one ingredient for producing enhanced bleaching when activated by electromagnetic energy.

12. The device for removing hair as set forth in claim 1, wherein the applicator includes a handle and the electromagnetic energy emission assembly is contained within the handle.

13. The device for removing hair as set forth in claim 1, wherein the energy emission assembly is configured to emit electromagnetic energy having an energy density from about 0.1 J/cm$^2$ to about 1.0 J/cm$^2$.

14. The device for removing hair as set forth in claim 1, wherein the energy emission assembly is constructed to emit electromagnetic energy which is substantially free of light that would cause heating of the skin.

15. The device for removing hair as set forth in claim 14, wherein the reservoir is filled with a composition for disrupting hair cuticles.

16. A method for removing hair comprising the following steps:

introducing a depilatory composition from an applicator onto a skin surface, wherein the depilatory composition comprises at least one of a thiol component and a ceteareth component; thereafter applying diffused electromagnetic energy to the skin surface where the depilatory composition has been introduced, wherein the electromagnetic energy is applied with an energy emission assembly, which is coupled to the applicator, for a duration of at least three seconds and wherein the diffused electromagnetic energy reacts with the depilatory composition to cause at least partial disruption of at least one of hair follicles and hair cuticles on the skin surface; and thereafter mechanically removing hair from the skin surface with a blade affixed to the applicator.

17. The method for removing hair according to claim 16, wherein the step of introducing a depilatory composition onto a skin surface comprises a step of introducing a depilatory composition comprising a thiol component and a ceteareth component.

18. The method for removing hair according to claim 17, wherein the step of introducing a depilatory composition onto a skin surface comprises a step of introducing a depilatory composition comprising a thiol component, a ceteareth component, water, a lubricant, a hydroxide component, a moisturizer, an aloe component and a fragrance.

19. The method for removing hair according to claim 18, wherein the lubricant comprises a mineral oil.

20. The method for removing hair according to claim 18, wherein the hydroxide component comprises at least one of a metal hydroxide, a sodium hydroxide, calcium hydroxide and a cetearylalcohol.

21. The method for removing hair according to claim 3, wherein the moisturizer comprises lanolin.

22. The method for removing hair according to claim 3, wherein the aloe component comprises at least one of an aloe juice, an aloe extract, and an aloe vera gel.

23. The method for removing hair according to claim 17, wherein the step of mechanically removing hair from the skin surface comprises a step of removing hair from the skin surface with a razor blade.

24. The method for removing hair according to claim 17, wherein the thiol component comprises at least one of a metal thioglycolate, a calcium thioglycolate, a sodium thioglycolate and a potassium thioglycolate.

25. The method for removing hair according to claim 17, wherein the ceteareth component comprises at least one of a cetearylalcohol and a ceteareth-20.

26. The method for moving hair according to claim 2, wherein the composition comprises water, a mineral oil, a calcium hydroxide, a ceaterylalcohol, a calcium thioglycolate, a sodium thioglycolate, a ceteareth-20, a lanolin, an aloe juice and a fragrance.

27. The method for removing hair according to claim 2, wherein the composition further comprises at least one of the following: a sodium silicate, a stearyl alcohol, a squalane, a tocopheryl acetate (vitamin B), an avocado oil, a jojoba oil, a bisabol, a sodium lauryl sulfate, a urea, and an iron oxide.

28. The method for removing hair according to claim 2, wherein the step of introducing the composition is affected by topical administration.

29. The method for removing hair according to claim 16, wherein the step of applying diffused electromagnetic energy comprises applying electromagnetic energy having an energy density from about 0.1 J/cm$^2$ to about 1.0 J/cm$^2$.

30. The method for removing hair according to claim 16, wherein the step of applying diffused electromagnetic energy comprises applying electromagnetic energy having an energy density from about 0.1 J/cm$^2$ to about 15 J/cm$^2$.

31. The method for removing hair according to claim 16, wherein the step of applying diffused electromagnetic energy comprises applying electromagnetic energy which is substantially free of light which would cause heating of the skin.

32. The method for removing hair according to claim 16, wherein the depilatory composition comprises a composition for disrupting hair cuticles.

* * * * *